United States Patent
Dexter et al.

(10) Patent No.: US 10,258,755 B2
(45) Date of Patent: Apr. 16, 2019

(54) TRANSITIONAL AIRWAY

(71) Applicants: Jeffrey Lee Dexter, Aiken, SC (US); John Paul Dexter, Darlington, SC (US)

(72) Inventors: Jeffrey Lee Dexter, Aiken, SC (US); John Paul Dexter, Darlington, SC (US)

( * ) Notice: Subject to any disclaimer, the term of this patent is extended or adjusted under 35 U.S.C. 154(b) by 0 days.

(21) Appl. No.: 15/828,743

(22) Filed: Dec. 1, 2017

(65) Prior Publication Data
US 2018/0353719 A1 Dec. 13, 2018

Related U.S. Application Data

(63) Continuation-in-part of application No. 15/619,508, filed on Jun. 11, 2017.

(51) Int. Cl.
*A61M 16/04* (2006.01)

(52) U.S. Cl.
CPC ........ *A61M 16/049* (2014.02); *A61M 16/0402* (2014.02); *A61M 16/0463* (2013.01); *A61M 2016/0413* (2013.01)

(58) Field of Classification Search
CPC .............. A61M 16/04; A61M 16/0402; A61M 16/0463; A61M 16/0475; A61M 16/0477; A61M 16/049; A61M 16/00; A61M 16/0465; A61M 16/0486; A61M 16/0497; A61M 16/0816; A61M 16/0833; A61M 16/085; A61M 25/0097; A61M 25/0108; A61M 2025/022; A61M 39/10; A61M 2039/1077; A61M 2205/32; A61B 1/267
USPC ....................................................... 600/194
See application file for complete search history.

(56) References Cited

U.S. PATENT DOCUMENTS

| | | | | |
|---|---|---|---|---|
| 3,927,676 A | * | 12/1975 | Schultz | A61M 25/02 128/207.17 |
| 4,584,998 A | * | 4/1986 | McGrail | A61M 16/04 128/207.15 |
| 4,681,100 A | * | 7/1987 | Brychta | A61M 16/0833 128/204.25 |
| 4,700,700 A | * | 10/1987 | Eliachar | A61M 16/04 128/207.15 |
| 4,953,547 A | * | 9/1990 | Poole, Jr. | A61M 16/0463 128/203.12 |

(Continued)

FOREIGN PATENT DOCUMENTS

DE 102014109001 A1 * 12/2015 ............ A61M 16/04

OTHER PUBLICATIONS

Omnexus, "Hardness Shore D"; retrieved from https://omnexus.specialchem.com/polymer-properties/properties/hardness-shore-d).*

(Continued)

*Primary Examiner* — Tan-Uyen T Ho
*Assistant Examiner* — Joseph D. Boecker
(74) *Attorney, Agent, or Firm* — Dale J. Ream

(57) ABSTRACT

A multi-functional oropharyngeal airway device designed to be inserted into the peripheral portion of a patient's oral airway to establish and maintain that airway. The components comprising the invention are a non-compressible, hollow cylinder body with at least three different and commonly used medical connectors incorporated into the proximal end of the body, and a flexible tube incorporated into the distal end of the body. The specific geometry and inclusion of the components of the airway device are arranged to be inserted and affixed into a peripheral position in a patient's mouth.

13 Claims, 6 Drawing Sheets

(56) References Cited

U.S. PATENT DOCUMENTS

| | | | |
|---|---|---|---|
| 5,181,508 A * | 1/1993 | Poole, Jr. | A61M 16/0463 |
| | | | 128/203.12 |
| 5,697,365 A * | 12/1997 | Pell | A61M 16/04 |
| | | | 128/207.14 |
| 5,873,362 A * | 2/1999 | Parker | A61M 16/04 |
| | | | 128/207.14 |
| 6,098,617 A | 8/2000 | Connell | |
| 7,278,420 B2 | 10/2007 | Ganesh et al. | |
| D613,854 S * | 4/2010 | Young | D24/112 |
| 2010/0163022 A1* | 7/2010 | Brewer | A61M 16/0463 |
| | | | 128/200.24 |
| 2013/0023729 A1* | 1/2013 | Vazales | A61B 1/0669 |
| | | | 600/104 |
| 2016/0256646 A1* | 9/2016 | Vazales | A61B 1/267 |
| 2016/0296719 A1* | 10/2016 | Geraghty | A61M 16/0486 |
| 2017/0049985 A1* | 2/2017 | Salcedo | A61M 16/085 |
| 2017/0281890 A1* | 10/2017 | Kang | A61M 16/00 |

OTHER PUBLICATIONS

Carin A. Hagberg, Carlos A. Artime, William H. Daily. "The difficult airway: A practical guide." Oxford University Press 2013; retrieved online from https://books.google.com/books?id=boVoAgAAQBAJ&Ipg=PA107&ots=_MiNiAyCef&dq=bull%20nosed%20ett%20vs.%20beveled%20ett&pg=PA107#v=onepage&q=bull%20nosed&f=false—only p. 107 attached.*

* cited by examiner

TRANSITIONAL AIRWAY

REFERENCE TO RELATED APPLICATIONS

This application claims the benefit of patent application Ser. No. 15/619,508 filed Jun. 11, 2017 titled Dexter Transitional Airway and which is incorporated in its entirety herein by reference.

BACKGROUND OF THE INVENTION

Proper airway establishment and management currently is problematic in all realms of the medical sphere, especially as concerns lesser-trained personnel. The plight of the Emergency Medical Technician (EMT) richly illustrates this point. In an emergency medical event, airway management is the most important factor in determining the survival and subsequent outcome of the patient. The majority of patients who are semiconscious or unconscious due to trauma, seizures, heart-attacks, drugs, alcohol, or a host of other causes will require this airway establishment and management to some degree. Under these conditions, muscles in the patients relax. When muscles in the mouth and throat begin to relax, the tongue tends to slide backward against the back of the throat causing an airway obstruction. When this occurs, the first step is to open the patient's airway through the use of manual positional adjustments. This includes chin lift, hyperextension of the head, and jaw thrust. If these maneuvers are unsuccessful or contraindicated, then the airway must be established by mechanical means (i.e., oropharyngeal airway, nasopharyngeal airway, laryngeal mask airway, or endotracheal tube).

The oropharyngeal airway (OPA) can be inserted into the mouth to establish an open passage to allow for airflow into the lungs. Since this device passes down the centerline of the tongue, it is centered on the largest of the gag reflexes at the uvula. As long as the patient does not regain consciousness and begin to vomit or gag (thereby obstructing the airway once again) things will be okay. However, acceptance of this device by the conscious patient is poor, and the possibility of dental damage is real.

The nasopharyngeal airway (NPA) is a device that is inserted into the nasal cavity until it reaches the upper pharyngeal region of the throat, just below the base of the tongue. It allows for oxygen flow past the obstruction produced by the tongue. Because the NPA is a somewhat intrusive procedure to delicate nasal tissues, it can cause nose bleed, hemorrhage or ulceration. If improperly inserted, it can inadvertently be routed into the patient's brain. It cannot be used in patients with such conditions as impaired blood-clotting, deviated septum, sinusitis, heavy nasal congestion, enlarged adenoids, and nasal trauma. When properly inserted, the NPA can stimulate the gag reflex and induce vomiting. Acceptance of this device by the conscious patient is poor.

The very high skill level required to place the laryngeal mask airway (LMA) and the endotracheal tube (ETT) is beyond the scope of most healthcare providers. In order to insert an ETT or LMA, the patient must totally unconscious. If this is not the case, the patient will have to be heavily sedated. Few healthcare providers are allowed to administer sedation drugs to a patient independently. The only options, at this point, is to wait until the patient deteriorates into total unconsciousness in order to insert the ETT or LMA, or await the arrival of higher skilled providers.

Once the patient's airway is established, respiratory status is evaluated to determine what level of management is required. Judgment of this by EMTs is highly subjective. "Is the patient breathing adequately?" is the criteria by which this judgement call is made. If the respiratory status appears normal, intervention may only involve administration of supplemental oxygen, possibly by use of the Nasal Cannula (NC). The NC is an oxygen tube with two prongs which insert into the immediate openings of the patient's nostrils. Some NCs even have provisions for $CO_2$ monitoring. They cannot, though, be used effectively in patients with certain conditions, including nasal trauma, sinusitis, enlarged adenoids, apnea and colds. Barring the restrictions of its use, the NC can provide a passive supply of oxygen and valuable monitoring of expired gases if the patient chooses to breathe through his or her nose. Sometimes that is not the case.

If the patient exhibits signs of impaired respiratory effort, the go-to device most commonly employed by healthcare professionals to provide positive airway pressure is the bag-valve mask (BVM). This device consists of a large, one-size-fits-all mask with a bag attached to it which, when squeezed with both hands, allows air to be forced into the lungs of the patient. In many cases, it takes two persons to operate this device—one to hold the mask down onto the patient's face and force the patient's jaw into the mask to form a complete seal, and the other to squeeze the bag. Other needed medical interventions to the patient cannot be addressed until the airway has been secured. Fully sealing the mask against the patient's face is key in this procedure, and it does take a fair amount of skill and practice to be able to do so. Certain factors, such as advanced age, obesity, absence of teeth, anatomical variations of the jaw or throat structure, cervical spine injury, and/or facial hair may add to the complexity of using a BVM, or even render it impossible to use. An agitated or claustrophobic patient fighting mask placement adds to the problems already listed. Even with proper usage, the mask can cause additional trauma to eyes (corneal abrasions). Excessive positive airway pressure from the BVM can result in damage to lung tissues, inflation of the stomach, vomiting, aspiration, and subsequent airway obstruction. Certain BVMs will allow for the monitoring of the patient's expired $CO_2$ gases. If the BVM can somehow be properly sealed and used in the first place, this valuable monitoring information can be used to improve the outcome of the patient.

Airway establishment and management problems do extend to other realms of the medical sphere, as well. The need for airway establishment and management may crop up any time in patients who are receiving sedation and/or pain management. These medications are routinely administered to patients as they undergo certain procedures in departments, such as Emergency Rooms, Catheterization Labs, Gastrointestinal Labs, Radiology Labs, etc. As mentioned before, any agent that induces relaxation of the muscles in the mouth can cause obstruction of the airway. Certain risk factors in the patient, including sensitivity and overreaction to sedatives or pain medication, obesity, infirmity, abnormal airway and obstructive sleep apnea increase the likelihood that airway obstructions will occur. When complications do arise, the procedure is halted until the complication has been resolved. In the case of procedures involving the use of the oral cavity as an entry point (such as GI Endoscopy) the procedure must sometimes be halted, and the tubes removed in order to address the problem. Typical resolution of these airway problems may involve the use of a mask (the problems of which have been previously discussed) to provide oxygen, along with an NPA to open the airway (the problems of which have also been previously discussed). If these attempts are unsuccessful, a person skilled in airway management must be summoned from another department to address the problem. Typically, the solution will involve the insertion of an ETT or LMA. Heavy sedation is required to paralyze the patient prior to this intubation. This is not always desirable in a routine procedure.

Persons administering anesthesia gases in the operating room often experience the same problems as those persons in other departments of the medical sphere. Current wisdom states that the depth and duration of anesthesia should be minimized as much as possible, especially for the very young and the elderly, in order to minimize the risks and complications therein. Oftentimes, though, the level of anesthesia is determined, not by the medical procedure being performed, but by the type of airway device that is being used. The use of ETTs and LMAs, and even traditional oropharyngeal airways requires deep sedation or paralysis of the patient. NPA type devices, with their previously discussed shortcomings, are an option, but they must be used in conjunction with a mask (the problems of which have been previously discussed, also).

Airway establishment and management problems may arise in the post-operative setting. The patient must be heavily sedated up to the time when ETTs or LMAs are removed. In the transitional period after removal of these devices, when the patient is being "weaned" off of anesthetic gases, it is determined whether the patient will be able breath on his or her own. Monitoring of oxygen saturation is routinely performed during this weaning period. There is, though, no 100% reliable way to monitor $ETCO_2$. Upon removal of the breathing tubes, if autonomous breathing does not occur, the BVM (with its attendant problems) must be deployed. The NPA (with its attendant problems) may also be deployed to keep the airway open. If the patient is too weak, and these strategies fail, the patient must be heavily sedated, and once again, the ETT or LMA must be re-inserted.

If the patient is successful in attaining autonomous breathing in the post-operative setting, pain medications are commonly administered. Because pain medications relax the tongue and throat muscles, in many circumstances, the patient's need for pain relieving drugs must be balanced against the need to keep the patient's airway open. Oftentimes, this results in the patient receiving much less pain relief than is needed.

Airway establishment and management problems, as mentioned above, extend to doctor's offices, clinics, outpatient spine treatment centers—they even extend to industrial and home emergency management. At most, the industrial or home first aid kit will include a mask and an oxygen bottle. At second best, it will contain a traditional oropharyngeal airway device. At worst, it will contain nothing, relying on EMTs to restore the airway. And, thus, we return to the beginning.

SUMMARY OF THE INVENTION

This invention is, in essence, a multi-purpose airway device designed to be inserted into the peripheral portion of a patient's oral airway to establish and maintain that airway. The components comprising the invention are a non-compressible plastic cylinder with, as the preferred construction directs, three different medical connectors at the proximal end. These connectors allow a multitude of medical procedures to be performed. Permanently attached to the distal end of the invention is a flexible tube. The novelty and the utility of this invention is that these components have not, heretofore, ever been incorporated into a single device which is inserted into a patient's mouth in such a manner.

Therefore, an object of this invention is to provide a stand-alone oropharyngeal airway device designed to establish the airway in patients when other methods fail or are not appropriate. As used in the manner to be discussed, the present invention is an unobtrusive and nonthreatening device which can be inserted into the patient's airway with little fear of invoking the gag reflex which is so common with other devices. Though mouth-to-mouth resuscitation in recent procedure directives for such has recently been discounted in the cardio-pulmonary resuscitation process, installation of this invention can greatly improve the chances of success with this procedure. Once installed into the patient, merely blowing into the device to provide life-sustaining air would greatly improve chances of survival.

Another object of the invention is to provide an oropharyngeal airway device, as aforesaid, in which an average person can be taught to use in less than 15 minutes, which takes less than 15 seconds to install into the patient, and which requires no sedatives or auxiliary equipment (such as laryngoscopes or fiber optic scopes) to properly install. In the pre-hospital setting, only one EMT is needed to install and utilize the device, freeing the other EMT to devote attention to other needed treatments. It is totally appropriate and of use in homes, industries, pre-hospital settings, clinics, doctor's offices, and in many spheres of the hospital setting.

Another object of the invention is to provide an oropharyngeal airway device which, in addition to merely establishing an airway can, by virtue of the three attachment ports on the upper body of the invention, provide a multitude of useful functions. Among these useful functions, positive airway pressure can be administered by attaching a bag-valve (from the BVM) to this device without fear of over-inflation of the lungs and subsequent injection of air into the esophagus and stomach. Once the device is installed, it is possible to provide positive air pressure to the patient by simply blowing air into the device via the mouth of the healthcare provider.

Still another object of the invention is to allow the use of more sophisticated procedures simultaneously through its attachment ports, such as bronchoscopy, administration of anesthetic gases, ventilation, nebulization, or administration of airway drugs (such as bronchodilators and topical anesthetics). By virtue of its placement on one side of the airway, the invention is totally compatible with the use of other independent medical procedures which utilize the center of the patient's oral opening, such as gastrointestinal endoscopy. When attached to anesthesia circuits, it allows for the least amount of sedation necessary while maintaining the airway. In post-operative settings, it allows for use of the optimum amount of pain-relieving drugs, while simultaneously maintaining the airway.

Other objects and advantages of the present invention will become apparent from the following description taken in connection with the accompanying drawings, wherein is set forth by way of illustration and example, embodiments of this invention.

BRIEF DESCRIPTION OF THE DRAWINGS

FIG. 2b is a sectional view taken along line 2b-2b of FIG. 2a;

FIG. 5b is an isolated view on an enlarged scale taken from a portion of FIG. 5a;

FIG. 6b is a sectional view taken along line 6b-6b of FIG. 6a;

FIG. 6c is an isolated view on an enlarged scale taken from a portion of FIG. 6a;

DESCRIPTION OF THE PREFERRED EMBODIMENT

Figure 1:
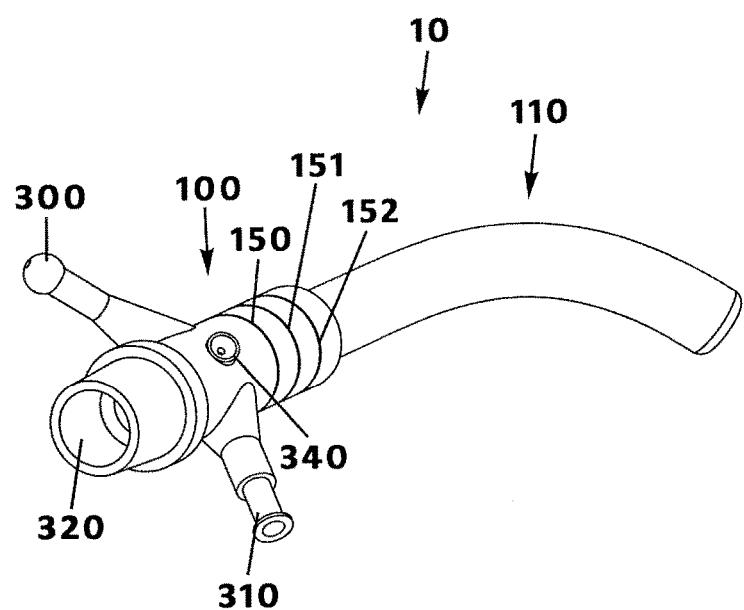
FIG. 1 is a perspective view of a transitional airway device according to a preferred embodiment of the present invention.
Figure 2A:
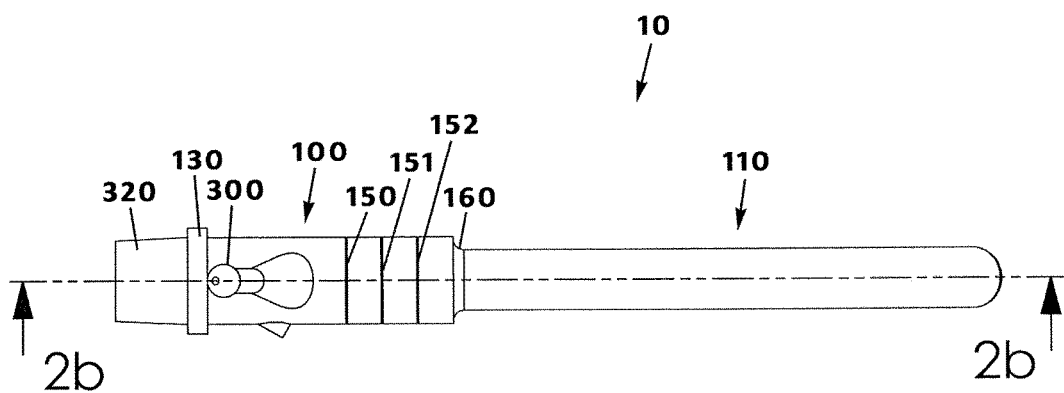
FIG. 2a is a side view of the transitional airway device as in FIG. 1.
Figure 2B:
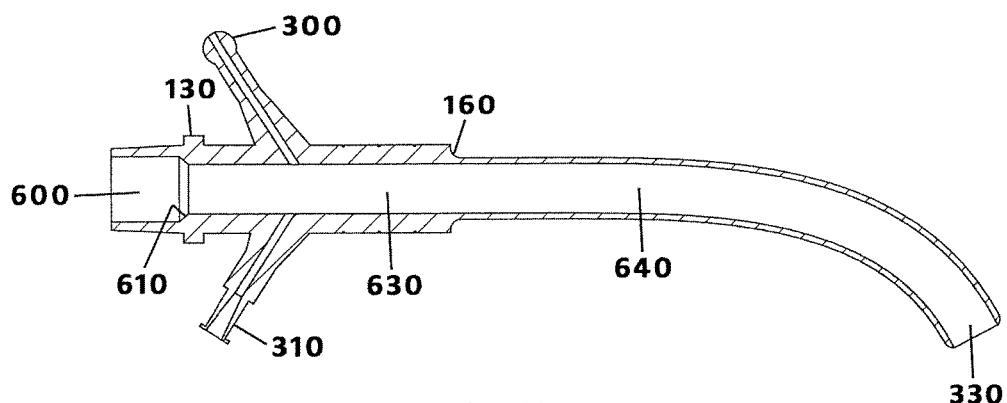
Figure 3:
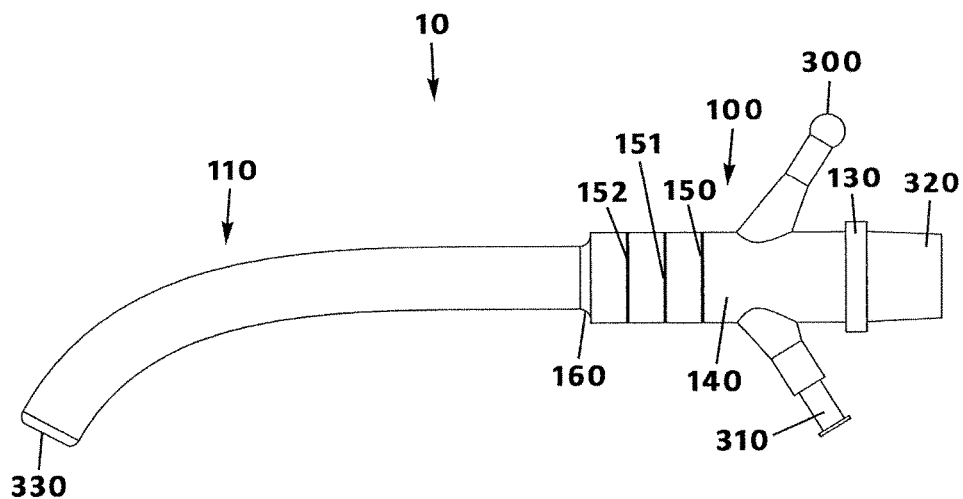
FIG. 3 is a top view of the transitional airway device as in FIG. 1.
Figure 4A:
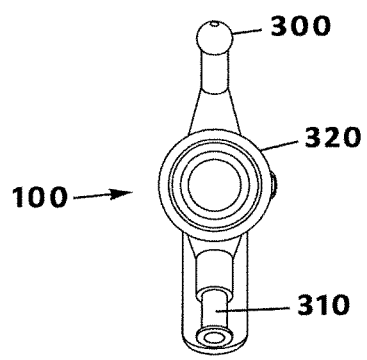
FIG. 4a is a proximal end view of the transitional airway device as in FIG. 3.
Figure 4B:
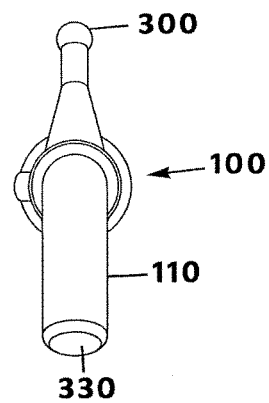
FIG. 4b is a distal end view of the transitional airway device as in FIG. 3.
Figure 5A:
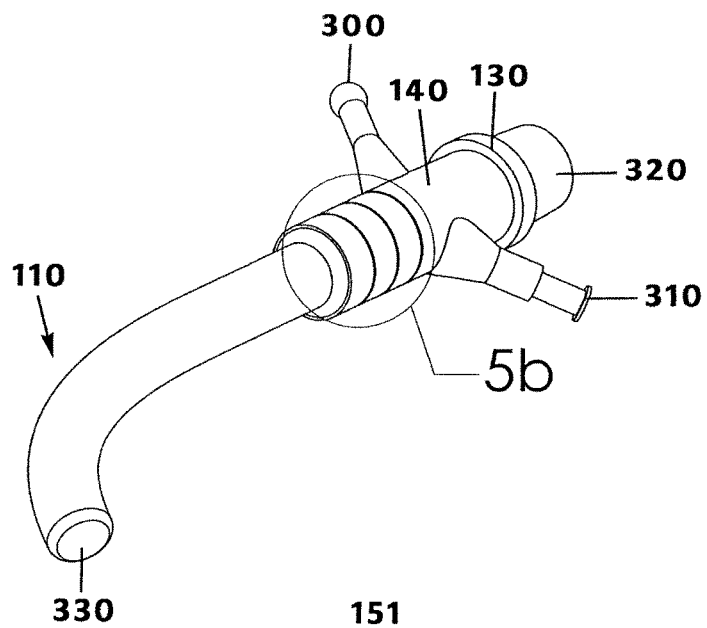
FIG. 5a is a perspective view from a reverse angle of the transitional airway device as in FIG. 1.
Figure 5B:
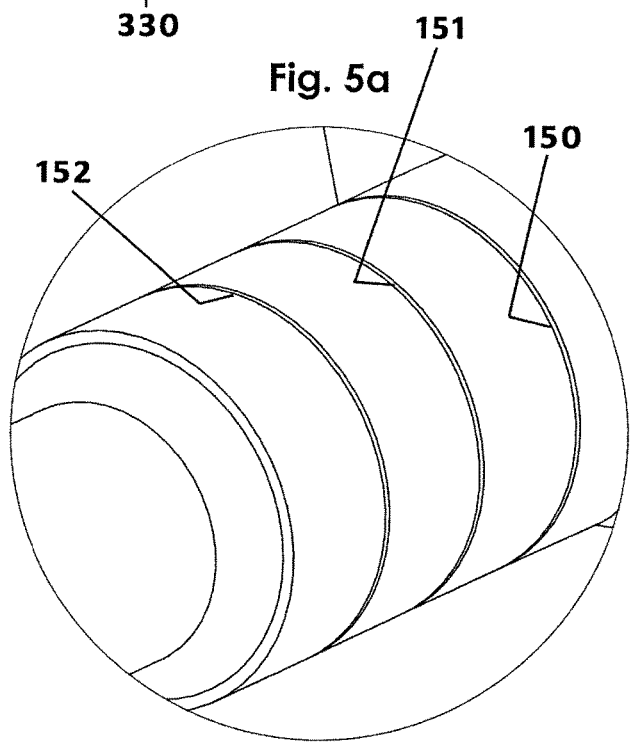
Figure 6A:
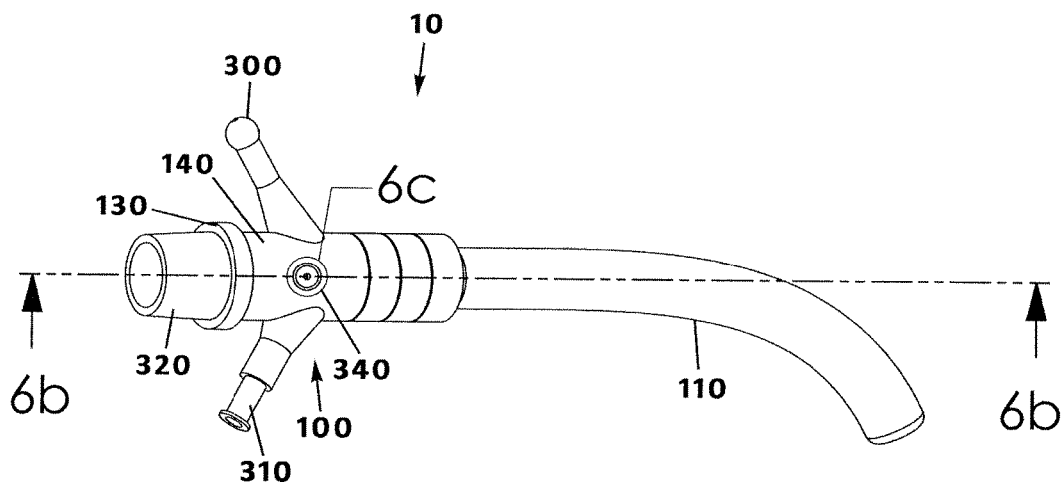
FIG. 6a is a top perspective view of the transitional airway device as in FIG. 1.
Figure 6B:
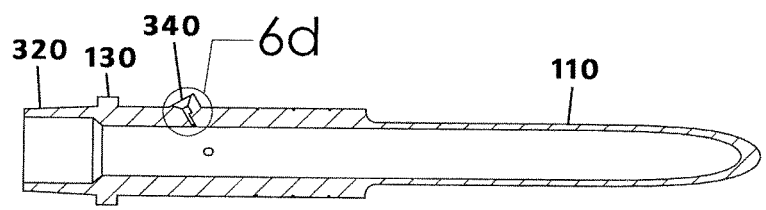
Figure 6C:
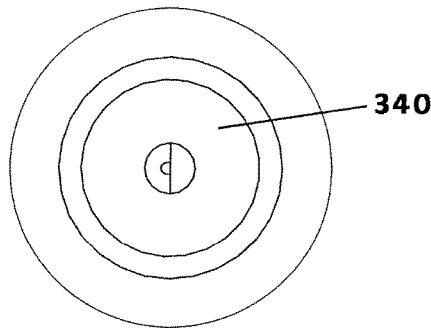
Figure 6D:
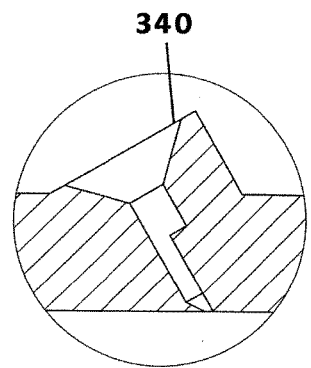
FIG. 6d is an isolated view on an enlarged scale taken from a portion of FIG. 6b.

An oropharyngeal airway device according to a preferred embodiment of the present invention will now be described with reference to FIGS. 1 to 8 of the accompanying drawings. The oropharyngeal airway device 10 includes a body portion 100 (also referred to merely as the "body") having connector ports (300, 310, 320) described below, and a delivery tube 110.

This invention is an oropharyngeal airway device, the body of which consists of a noncompressible cylinder, which will also be referred to below and in the claims as a body portion. In the preferred construction, there are four components incorporated onto this cylinder:

1. A standard 15 mm or 22 mm (ANSI/ISO) taper connector is incorporated into the terminal of the proximal end of the cylinder (referred to as a terminal connector 320).
2. A female 6% Luer-lock (ANSI/ISO) connector is incorporated on one side of proximal end the cylinder (referred to as a first lateral connector 310).
3. A standard ball or single barb oxygen tube connector is incorporated on the other side of the proximal end of the cylinder (referred to as a second lateral connector 300).
4. A flexible nasopharyngeal airway-type tube (minus the "trumpet" feature) is incorporated at the distal end of the cylinder as the delivery device.

Figure 7:
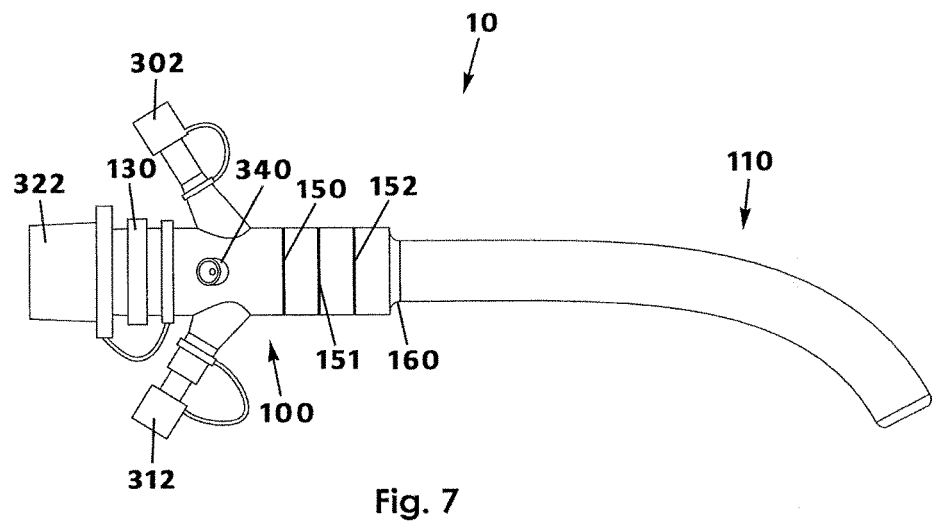
FIG. 7 is another top view of the transitional airway device illustrated with protective caps in sealed configuration on respective connectors.
Figure 8:
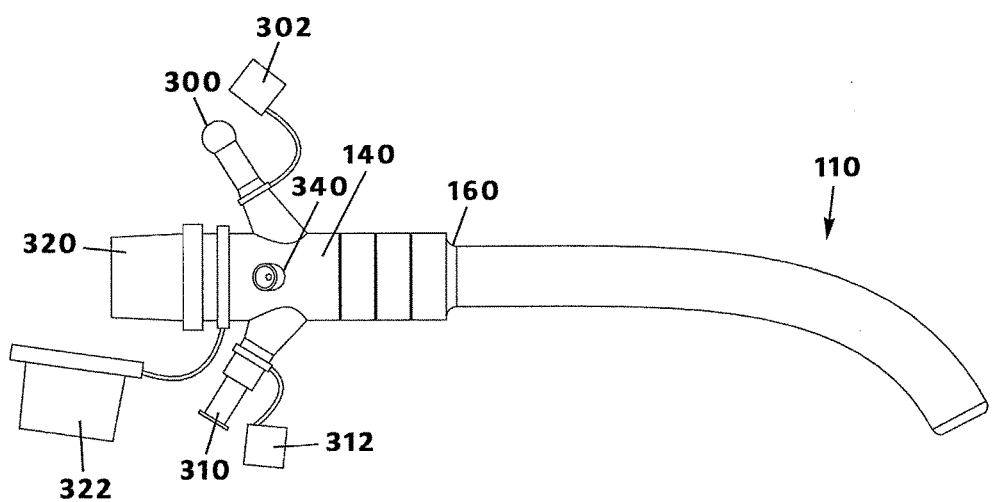
FIG. 8 is a top view of the transitional airway device as in FIG. 7 illustrated with protective caps in released configurations, respectively.

Appropriate caps 302, 312, 322 may be provided as seals for components 1 through 3 listed above (FIGS. 7 and 8). They may be separate or attached to the body portion 100, as needed. In the preferred embodiment, the non-compressible body 100 and connectors 300, 310, 320 are a single unit and have a unitary construction, such as injection molded of an FDA-approved plastic of sufficient hardness to withstand the pressures needed to attach and detach components to and from the two side connectors 300, 310 without bending or breakage of the connectors, and of sufficient body hardness to be able to withstand compression by a patient's teeth. A Shore 70D to 90D plastic, such as HDPE or 6/6 Nylon are possible choices for this application. Alternatively, a metal or graphite core, consisting of connectors 300, 310 and 320 and body portion 100, could be constructed with the main body portion to be subsequently coated with a highly-plasticized PVC, silicon or other suitable material. The optimal outer diameter along the length of the non-compressible body portion 100 below the terminal connector 320 and rib 130 is, but not limited to, 15 mm. The main or terminal connector 320 at the proximal end may be a standard 15 mm (ANSI/ISO) male connector, though a 22 mm (ANSI/ISO) male connector could alternately be manufactured into the device. The preferred length of the terminal connector 320 is 17 mm, below which a preferred 3 mm wide rib 130 is molded into the outer body. The inner diameter 600 corresponding to the 15/22 mm connector is, for the most part, arbitrary. The main consideration with this inner diameter is the ultimate strength of the 15/22 mm connector. A 13 mm inner diameter would be fully sufficient. If warping of the 15/22 mm taper is a problem in the manufacturing process, this inner diameter could be increased to make the male taper flexible enough to conform to the female taper fitting being used. From the larger inner diameter at the top 600, in a preferred construction, there is a transition area 610 consisting of a 30 to 45 degree angle (as measured from the centerline of the body) which leads down to the body inner diameter 630. This body inner diameter is dependent on, and the same, as the inner diameter 640 of the flexible tube 110 which is incorporated at the distal end of the body portion 100.

One of the lateral connectors (i.e. the second lateral connector 310) at the proximal end may be an (ANSI/ISO) 6% female Luer-lock connector. The other outer lateral connector (i.e. the first lateral connector 300) comprises a standard ball or single barb male oxygen tube connector. Both of these outer fittings 300, 310 have approximate 4 mm inner diameter holes 620 through them, connecting them with the channel of the body having inner diameter 630; both may incorporate fillets, radii, or angles at their base, at a suggested 5 mm, or less, in height, to reinforce their strength. Preferred length of the two lateral connectors 300, 310, as measured from the outer surface of the body, is 15 mm. Using 6/6 nylon or metal as the construction material, this length can be extended upwards of 20 mm. Using a softer material such as HDPE, this length should remain in the 15 mm range, and a 5 mm reinforcing radius or fillet may be constructed into the base of the lateral connectors 300, 310. The preferred centerline location of the two lateral connectors 300, 310 along the body of the device is about 10 mm below the rib 130. The particular positioning of the lateral connectors is critical in that they do not interfere with the use or function of the 15/22 mm terminal connector 320. Alternate or additional lateral connectors may be incorporated into the device if needed. In this regard, the drawings show an "auxiliary lateral connector" designated as 340.

Below the outer base of the two lateral connectors 300, 310 is a suggested 14 mm long area 140 along the body of the device designated as the "taping area." This is the area where standard ½" adhesive tape can be applied to affix the device to the face of the patient after the tube has been inserted to the proper depth in the airway. Alternate means of affixing the invention to the patient may be devised using this area. To be sure, the taping area is a structural and functional component of the present invention.

In the preferred embodiment, immediately below the taping area is a line 150 marked on or molded into the plastic, referred to as the "first graduation line." This line will be numbered, and this number will reflect the distance, in millimeters, from the aforementioned first graduation line 150 to the tip 320 of the flexible tube 110. That number on the first graduation line 150 will define the various sizes of the invention to be made available. Below the first graduation lines, additional graduation lines 151 and 152 are preferred at 10 mm increments, with each of these being, likewise, marked with their distance to the tip 330 of the flexible tube 110. In addition, the transition area 160 between the rigid body 100 and flexible tube 110 may consist of a smaller diameter extension (barbed, or otherwise) on which to UV bond, mold, or otherwise attach the flexible tube 110. The outer surface of this transition area 160 has a smooth surface. The angle of the transition should be as minimal as possible, as measured from the centerline of the body. In the preferred construction, the non-compressible body length between the first graduation line 150 and the beginning of the flexible tube 110 will vary with patient size, usually between 40 and 55 mm. It is intended that the non-compressible area of the invention extends slightly beyond the back molars when inserted into a patient's mouth so as to preclude compression of the flexible tube 110 by the teeth.

The flexible tube 110 at the distal end of the device 10 is of the same hardness, composition and construction as nasopharyngeal airway tubes, except that the flared stopper has been omitted from its construction. Suitable materials for this tube include plasticized PVC, polyurethane, and silicon. An anatomical Magill curve is incorporated into entire length of the flexible tube 110 for ease of insertion into the patient. The plane of this bend should be substantially similar as the plane which bisects both the cylindrical body and the side connectors. In another aspect, a plurality of radio-opaque markings is desired along the length of this tube 110 for detection with x-ray equipment. A bull-nosed distal tip 330 configuration is most desirable for ease of routing into the airway, but a smooth, beveled tip will work as well.

The proper length of the conventional nasopharyngeal airway (NPA) is determined by measuring the outer distance from the tip of the patient's nose to the tip of the earlobe. Similarly, the size of this invention is determined using that same patient nose-to-earlobe distance. Different sizes of this invention may exist for different nose-to-earlobe distances, and that size, as previously mentioned, will be reflected by the number on the first graduation line 150. With the conventional NPA, the length of the device also defines what the inner and outer diameter of the tube will be. This invention ideally follows those same conventions. The preferred construction of this invention would include at least the three sizes outlined in the table below:

| PATIENT SIZE | TUBE ID | TUBE OD | FRENCH NUMBER |
| --- | --- | --- | --- |
| Small Adult | 130 mm | 6.5 mm | 8.7 mm 26 |
| Medium Adult | 150 mm | 7.5 mm | 10 mm 30 |
| Large Adult | 170 mm | 8.5 mm | 11.3 mm 34 |

As earlier suggested, the internal diameter of the non-compressible body 630 should be one and the same as the tube internal diameter 640 that is being used. Other sizes of the invention may be constructed, if desired, by interpolation of the sizes listed above, and by consultation of the different sizes used for conventional NPA devices.

The Method of Use of the Device

In use, the installation of this device into the patient's airway is straightforward and can be learned in a short period of time. First, the size of device is determined by measuring the distance from the tip of patient's nose to the tip of his earlobe. The appropriate-sized device is chosen. The cap is removed from the top 15 mm connector. The patient's cheek (on the side of the mouth where the device is to be inserted) is pulled outward.

With the arc of the tube in an upward position, the terminal tip of the flexible tube is routed into that side of the oral cavity along the lower jaw, between the cheek and gums, until the terminal tip is beside the back-most molar. The device is then rotated 90 degrees so that the arc of the tube faces toward the tongue. The terminal tip is routed behind the back-most molar until it reaches the side of the tongue. From that point, the device is rotated another 90 degrees so that the arc of the tube is facing downward. The terminal tip of the tube is then routed down the channel beside the tongue and into the throat, until it is just past the base of the tongue and into the upper pharynx. For a patient with an obstructed airway, it is at this point that restored breathing will be able to be detected through the device. When this depth of insertion has been accomplished, the device is then taped to the patient's face. Preferably, taping is done up the cheek opposite to the side that the device has been inserted, then across the upper or lower lip area. The tape is then wrapped around the device, then down the cheek on the side in which the device has been inserted. Other means of affixing the invention could be devised. When the device is inserted in the manner described above, there is a likelihood that the uvular and tonsillar gag reflex areas will be bypassed, thereby reducing the risks associated with patient vomiting. If it should happen that the patient is able to bite down on the device after installation, the hard body 100 of the device will act as a bite block. Since the device is installed on the side of the mouth, only the stronger molars will be involved in biting, and the risk of breakage of the more fragile incisors will be eliminated. After inserting and affixing the device, it can be left as is, or peripheral devices can be immediately be connected to it to provide positive air pressure, monitor $ETCO_2$ readings, administer oxygen, etc.

It is understood that while certain forms of this invention have been illustrated and described, it is not limited thereto except insofar as such limitations are included in the following claims and allowable functional equivalents thereof.

The invention claimed is:

1. An oropharyngeal airway device for establishing and maintaining the airway of a patient, comprising:
    a body portion having a proximal end and a distal end opposite said proximal end, said body portion having a tubular configuration defining an interior channel and having a continuous side wall constructed of a non-compressible material;
    a terminal connector connected to said proximal end of said body portion and in-line with said channel, said terminal connector having an open end;
    a first lateral connector in fluid communication with said channel of said body portion and extending away from said body portion at an angle and in the direction toward said proximal end;
    a second lateral connector in fluid communication with said channel of said body portion and extending away from said body portion at an angle and in the direction toward said proximal end, said second lateral connector being displaced from said first lateral connector;

wherein said first and second lateral connectors have tubular configurations, respectively, for connection to medical equipment; and a tube having a first end connected to said distal end of said body portion and having a second end opposite said first end that has an open tip, said tube constructed of a flexible material and defining an anatomical Magill curve between said first end and said second end;

wherein an outer surface of said side wall of said body portion includes a plurality of graduation markings extending circularly and laterally about said body portion and spaced apart from one another.

2. The oropharyngeal airway device as in claim 1, wherein said outer surface of said side wall of said body portion includes a taping area situated between said first lateral connector, said second lateral connector, and said plurality of graduation markings, said taping area having a configuration for receiving an adhesive tape without interference.

3. The oropharyngeal airway device as in claim 1, further comprising a rib extending about said body portion and displaced a predetermined distance from said proximal end of said body portion, said rib extending outwardly from said body portion.

4. The oropharyngeal airway device as in claim 3, wherein said first and second lateral connectors are situated downstream from said rib and from said terminal connector.

5. The oropharyngeal airway device as in claim 1, wherein:
said channel of said body portion defines a channel diameter;
said tube defines a tube diameter that s smaller than said channel diameter;
said body portion includes a transition portion that is tapered from said channel diameter to said tube diameter.

6. The oropharyngeal airway device as in claim 1, wherein said body portion, said terminal connector, said first lateral connector, and said second lateral connector have a unitary construction and constructed of a plastic having a Shore durometer of 70D to 90D.

7. The oropharyngeal airway device as in claim 1, wherein said open tip of said second end of said tube is a bull-nosed distal tip for routing air from said tube to the airway of the patient.

8. The oropharyngeal airway device as in claim 1, wherein said open tip of said second end of said tube has a beveled tip configuration for routing air from said tube to the airway of the patient.

9. The oropharyngeal airway device as in claim 1, wherein said tube includes a plurality of radio-opaque markings coupled to and distributed along the length of said tube, said radio-opaque markings being detectable with x-ray equipment.

10. An oropharyngeal airway device for establishing and maintaining the airway of a patient, comprising:
a body portion having a proximal end and a distal end opposite said proximal end, said body portion having a tubular configuration defining an interior channel and having a continuous side wall constructed of a non-compressible material;
a terminal connector connected to said proximal end of said body portion and in-line with said channel, said terminal connector having an open end;
a first lateral connector in fluid communication with said channel of said body portion and extending away from said body portion at an angle and in the direction toward said proximal end;
a second lateral connector in fluid communication with said channel of said body portion and extending away from said body portion at an angle and in the direction toward said proximal end, said second lateral connector being displaced from said first lateral connector;
wherein said first and second lateral connectors have tubular configurations, respectively, for connection to medical equipment;
a tube having a first end connected to said distal end of said body portion and having a second end opposite said first end that has an open tip, said tube constructed of a flexible material and defining an anatomical Magill curve between said first end and said second end;
said terminal connector is an ANSI/ISO male connector;
said first lateral connector is a female 6% Luer-lock connector; and
said second lateral connector is one of a ball or single barb oxygen tube connector.

11. A method of for establishing and maintaining the airway of a patient, comprising:
inserting an oropharyngeal airway device into a mouth of the patient, said oropharyngeal airway device including:
a body portion having a proximal end and a distal end opposite said proximal end, said body portion having a tubular configuration defining an interior channel and having a continuous side wall constructed of a non-compressible material;
a terminal connector connected to said proximal end of said body portion and in-line with said channel, said terminal connector having an open end;
a first lateral connector in fluid communication with said channel of said body portion and extending away from said body portion at an angle and in the direction toward said proximal end;
a second lateral connector in fluid communication with said channel of said body portion and extending away from said body portion at an angle and in the direction toward said proximal end, said second lateral connector being displaced from said first lateral connector;
wherein said first and second lateral connectors have tubular configurations, respectively, for connection to medical equipment; and
a tube having a first end connected to said distal end of said body portion and having a second end opposite said first end that has an open tip, said tube constructed of a flexible material and defining an anatomical Magill curve between said first end and said second end;
wherein said side wall of said body portion includes a plurality of graduation markings extending circularly and laterally about said body portion and spaced apart from one another.

12. The method as in claim 11, further comprising the step of taping said oropharyngeal airway device to a cheek of the patient's mouth.

13. The method as in claim 11, wherein said outer surface of said side wall of said body portion includes a taping area situated between said first lateral connector, said second lateral connector, and said plurality of graduation markings, said taping area having a configuration for receiving an adhesive tape without interference.

* * * * *